United States Patent [19]

Kapa

[11] Patent Number: 4,841,071
[45] Date of Patent: Jun. 20, 1989

[54] 6-SUBSTITUTED-4-HYDROXY-TETRAHYDROPYRAN-2-ONES

[75] Inventor: Prasad K. Kapa, Parsippany, N.J.

[73] Assignee: Sandoz Pharm. Corp., E. Hanover, N.J.

[21] Appl. No.: 771,809

[22] Filed: Sep. 3, 1985

Related U.S. Application Data

[62] Division of Ser. No. 512,163, Jul. 8, 1983, Pat. No. 4,571,428.

[51] Int. Cl.$^4$ .................... C07D 313/00; C07D 313/04
[52] U.S. Cl. ...................................... 549/214; 549/271
[58] Field of Search ............................. 549/214, 271

[56] References Cited

U.S. PATENT DOCUMENTS

| | | | |
|---|---|---|---|
| 3,418,290 | 12/1968 | Bantjes et al. | 549/271 X |
| 4,376,733 | 3/1983 | Frimer | 549/271 X |
| 4,610,826 | 9/1986 | D'Angelo et al. | 549/271 X |

*Primary Examiner*—Paul F. Shaver
*Attorney, Agent, or Firm*—Gerald D. Sharkin; Richard E. Vila; Joanne M. Giesser

[57] ABSTRACT

6-Substituted-4-hydroxy-tetrahydropyran-2-ones, useful as anti-atherosclerotic agents, are obtainable by the process of the invention. The 6-substituents have a phenyl, naphthyl, tetrahydronaphthyl or indolyl nucleus bound through an ethenyl unit. The invention includes novel intermediates.

6 Claims, No Drawings

6-SUBSTITUTED-4-HYDROXY-TETRAHYDROPY-RAN-2-ONES

This is a division of application Ser. No. 512,163, filed July 8, 1983, now U.S. Pat. No. 4,571,428.

This invention relates to a process for preparing organic compounds, and more specifically for preparing 6-substituted-4-hydroxy-tetrahydropyran-2-ones, as well as intermediates, per se in the process.

This invention provides a novel process for the preparation of trans olefins of the formula I:

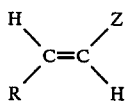

wherein R is:
a phenyl structure of formula A:

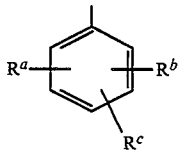

in which each of the $R^a$, $R^b$ and $R^c$ is independently hydrogen; halogen; $C_{1-4}$ alkyl; $C_{1-4}$ haloalkyl; phenyl, or phenyl substituted by halogen, $C_{1-4}$ alkoxy, $C_{2-8}$ alkanoyloxy, $C_{1-4}$ alkyl or $C_{1-4}$ haloalkyl, or $OR^d$ in which $R^d$ is any of hydrogen, $C_{2-8}$ alkanoyl, benzoyl, phenyl, halophenyl, phenyl $C_{1-3}$ alkyl, $C_{1-9}$ alkyl, cinnamyl, $C_{1-4}$ haloalkyl, allyl, cycloalkyl-$C_{1-3}$ alkyl, adamantyl-$C_{1-3}$ alkyl, or substituted phenyl-$C_{1-3}$ alkyl in each of which the substituents are selected from the group consisting of halogen, $C_{1-4}$ alkoxy, $C_{1-4}$ alkyl, or $C_{1-4}$ haloalkyl;

a naphthyl or tetrahydronaphthyl structure of formula B:

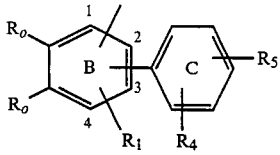

wherein the two $R_o$ groups together form a radical of the formula

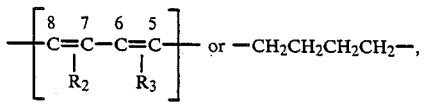 or $-CH_2CH_2CH_2CH_2-$, wherein
$R_2$ is hydrogen, $C_{1-3}$ alkyl, n-butyl, i-butyl, $C_{1-3}$ alkoxy, n-butoxy, i-butoxy, trifluoromethyl, fluoro, chloro, phenoxy or benzyloxy,
$R_3$ is hydrogen, $C_{1-3}$ alkyl, $C_{1-3}$ alkoxy, trifluoromethyl, fluoro, chloro, phenoxy or benzyloxy, with the provisos that not more than one of $R_2$ and $R_3$ is trifluoromethyl, not more than one of $R_2$ and $R_3$ is phenoxy, and not more than one of $R_2$ and $R_3$ is benzyloxy, $R_1$ is hydrogen, $C_{1-3}$ alkyl, fluoro, chloro or benzyloxy,
$R_4$ is hydrogen, $C_{1-3}$ alkyl, n-butyl, i-butyl, $C_{1-3}$ alkoxy, n-butoxy, i-butoxy, trifluoromethyl fluoro, chloro, phenoxy or benzyloxy,
$R_5$ is hydrogen, $C_{1-3}$ alkyl, $C_{1-3}$ alkoxy, trifluoromethyl, fluoro, chloro, phenoxy or benzyloxy, with the provisos that not more than one of $R_4$ and $R_5$ is trifluoromethyl, not more than one of $R_4$ and $R_5$ is phenoxy, and not more than one of $R_4$ and $R_5$ is benzyoloxy, with the proviso that the single bond on ring B and that of the $R_4$-bearing the phenyl group (ring C) are ortho to each other; or an indolyl structure of the formula C:

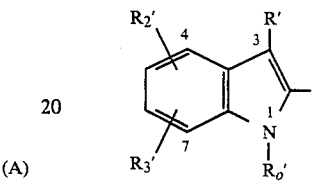

wherein
one of R' and $R_o'$ is

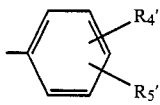

and the other is $C_{1-3}$ alkyl, n-butyl or i-butyl, wherein
$R_4'$ is hydrogen, $C_{1-3}$ alkyl, n-butyl, i-butyl, $C_{1-3}$ alkoxy, n-butoxy, i-butoxy, trifluoromethyl, fluoro, chloro, phenoxy or benzyloxy, and
$R_5'$ is hydrogen, $C_{1-3}$ alkyl, $C_{1-3}$ alkoxy, trifluoromethyl, fluoro, chloro, phenoxy or benzyloxy, with the proviso that not more than one of $R_4'$ and $R_5'$ is trifluoromethyl, not more than one of $R_4'$ and $R_5'$ is phenoxy and not more than one of $R_4'$ and $R_5'$ is benzyloxy $R_2'$ is hydrogen, $C_{1-3}$ alkyl, n-butyl, i-butyl, $C_{1-3}$ alkoxy, n-butoxy, i-butoxy, trifluoromethyl, fluoro, chloro, phenoxy or benzyloxy, $R_3'$ is hydrogen $C_{1-3}$ alkyl, $C_{1-3}$ alkoxy, trifluoromethyl, fluoro, chloro, phenoxy or benzyloxy with the provisos that not more than one of $R_2'$ and $R_3'$ is trifluoromethyl, not more than one of the $R_2'$ and $R_3'$ is phenoxy, and not more than one of $R_2'$ and $R_3'$ is benzyloxy, and Z is

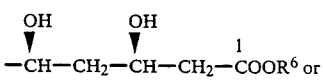

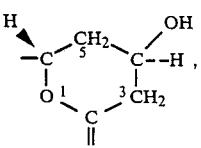

wherein $R^6$ is hydrogen, $C_{1-3}$ alkyl, n-butyl, i-butyl, t-butyl, benzyl or M, wherein M is a pharmaceutically acceptable cation;* provided that when R is of type A, Z is not of type II.

*i.e., the resulting salt is non-toxic and pharmaceutically acceptable.

The compounds of formula I constitute 3 classes of compounds depending on the nature of R, namely (1) compounds IA, where R is of formula A, IB where R is of formula B, and of IC when R is of formula C. Within the main classes, subclass can be seen, such as type IB-1 where $R^0+R^0$ is an alkadienyl chain and type IB-2 where $R^0+R^0$ is a alkylene chain; types IC-1 and IC-2 depending upon whether $R^0$ is at position-1 or-3.

Compounds IA are known and described in U.S. Pat. No. 4,308,378 (issued Dec. 29, 1981) wherein the compounds are disclosed to be useful as anti-hypercholesteremic agents. Compounds IB are disclosed in pending application Ser. No. 460,600 filed Jan. 24, 1983. Compounds IC are disclosed in pending application Ser. No. 443,668 filed Nov. 22, 1982. Compounds IB and IC are also useful an anti-hypercholesteremic agents as they are inhibitors of cholesterol biosynthesis in the manner of the known products compactin and mevinolin and are therefore useful in the treatment of atherosclerosis, as described in said applications.

The terms "halogen" and "halo" as used in the definition of compounds IA is intended to include fluoro and chloro.

An embodiment of this invention is a multi-step process for the preparation of compounds I, which process may conveniently be represented by Reaction Scheme A, below, wherein R is as defined above. $R^{6'}$ is the same as $R^6$ when it is not hydrogen or M and P' is a protecting (or masking) group for a hydroxy function. The final products I are shown as compounds I' (where Z is of type II and $R^6$ is $R^{6'}$, I'' where $R^6$=H or M, and I''' where Z is of type III.

REACTION SCHEME A

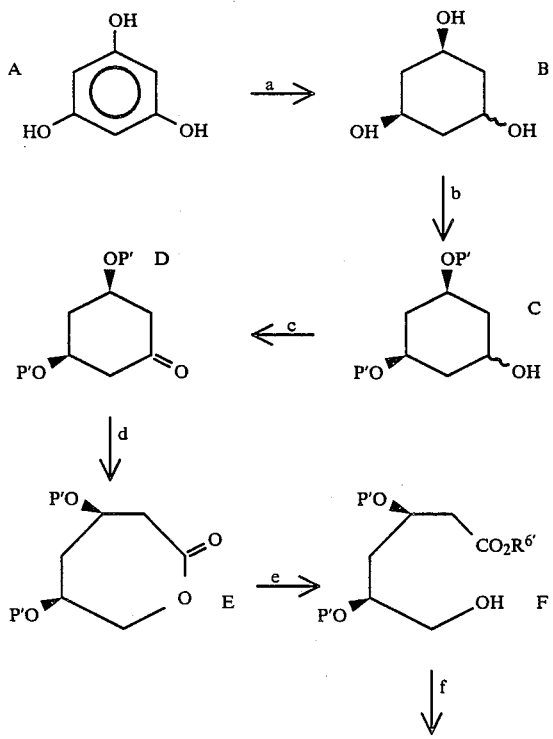

-continued
REACTION SCHEME A

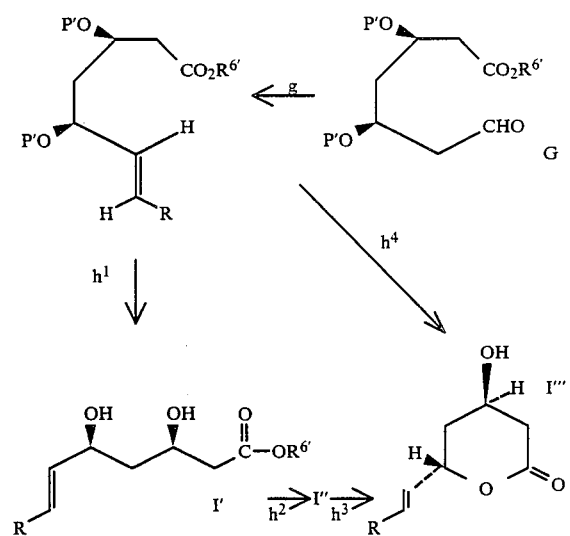

Referring to Reaction Scheme A, above compounds A and B are known. Compounds C, D, E, F, G and H are novel and also comprise an embodiment of this invention. A particularly interesting embodiment of this invention is the deprotection/cyclization of a compound H to its corresponding compound I''' in a single vessel.

Another interesting embodiment of this invention is the preparation of compounds H by reaction of an aldehyde (compound G) with a reagent furnishing the moiety

—CH=CH—R in which R is as defined above. It is surprisingly unexpected that the reaction (process g) provides the trans isomer product (H) in high yields. It is also particularly interesting that the above reaction scheme provides the di-protected product (G) in high yields as a single diastereo isomer. Accordingly, each of the process steps (b) to $h^4$ and the reaction products thereof, individually and in combination, constitute embodiments of this invention.

In process (a) phloroglucinol (Compound A) is reduced to 1,3,5-trihydroxycyclohexane (a compound B). The reduction may be accomplished by conventional means for reducing an aromatic compound to its saturated analog. A convenient method of carrying out process (a) is by hydrogenation under moderate pressure, e.g., from about 15 to 75 psi, such as 50 psi, in the presence of a hydrogenation catalyst, e.g., Raney Nickel or 5% rhodium on alumina at moderate temperatures, e.g., 20° to 80° C., such as 50° C., under essentially anhydrous contitions, in an inert medium, e.g., a lower alcohol, e.g., ethanol, or acetic acid 15% in ethanol.

Where one of the isomers of compound B is obtained in which all hydroxy groups are in the cis relationship to each other, i.e., a compound B',

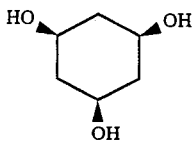

such may be used as a precursor to compound C by treatment analogous to processes (b) and (c) hereinafter described. However, it is preferred to use a compound B″ in which two of the hydroxy groups are in cis-relationship and the third is trans-thereto, as such isomer gives higher yields of the di-protected product (C), whereas the cis triol tends to give a significant amount of the undesirable tri-protected product.

In process (b), a compound B is converted to a corresponding compound C by conversion of two of the hydroxy functions to protected forms. Process (b) may be accomplished by reacting a compound B with at least 2 equivalents thereof of a protecting group-bearing reagent of the formula II:

$$P'-L \qquad\qquad II$$

in which P' is as defined above and L is a leaving group, in the presence of an acid acceptor, e.g., imidazol, in an inert medium, e.g., a liquid amide, such as dimethyl formamide (DMF) at moderate temperatures, e.g., from about 5° to 40° under essentially anhydrous conditions. The preferred compound II is chloro-diphenyl-t-butyl-silane. Leaving groups are well known in the art, and include higher halo, i.e., chloro, bromo, or iodo, preferably chloro, and alkyl and aryl sulfonyl, radicals, e.g., $C_1$-$C_6$ alkyl or phenyl which may be substituted or mono-substituted by a $C_1$-$C_4$ alkyl, such as p-toluene sulphonyl.

Suitable protective groups P', include (1) tri-substituted silyl radicals have at least 2, and preferably 3 bulky radicals, i.e. radicals selected from the group consisting of (a) tertiary alkyl ($C_4$ to $C_8$) groups especially t-butyl, and (b) aryl, preferably phenyl which may be unsubstituted or substituted by up to 2 (preferably 0 or 1) of any of lower alkyl ($C_1$-$C_4$), chloro, nitro, trifluoromethyl, or mono-substituted in the para-position by phenyl or benzyl (which may be unsubstituted or in turn substituted by one or two of such groups as mentioned above, especially at the para-position; or (2) benzyl which may be unsubstituted or substituted by one or two (preferably only one, and at the para-position) of lower alkoxy ($C_1$-$C_4$) e.g., methoxy, chloro, nitro, or lower alkyl ($C_1$-$C_6$), or mono-substituted in the para-position by phenyl or benzyl, which may be unsubstituted or may in turn be substituted by one or two of the groups mentioned above.

In process (c), the free hydroxy function of a compound C is oxidized to a carbonyl function to obtain a corresponding compound D. The oxidation may be carried out by the conventional manner for oxidizing a hydroxy to a carbonyl function. A convenient method of accomplishing process (C) is to treat a compound C with pyridinium chlorochromate, under essentially anhydrous conditions by employing molecular sieves, at moderate temperatures, e.g., from 20° to 60° C., such as 20° to 30° C., in an inert medium, such as a chlorinated lower alkane, e.g., methylene chloride, i.e. dichloro-methane.

In process(d), a compound D is converted to its corresponding 7-member-ring lactone (a compound E), by a Baeyer-Villiger oxidation employing m-chloroperbenzoic acid and an inorganic base such as anhydrous sodium bicarbonate, under essentially anhydrous conditions at moderate temperatures, e.g. from about 20° to 100° C., such as at the reflux temperature of the mixture, in an inert medium, e.g., a chlorinated lower alkane, such as methylene chloride. It is convenient to subject the mixtures to ultrasonic radiation, but this is not essential.

In process (e), a compound E (lactone) is opened by reacting with an alcohol of the formula $R^{6'}$—OH, in which $R^{6'}$ is as defined above, in the presence of a catalytic amount, e.g. 1%, of an acid, e.g., trifluoroacetic acid, acetic acid or hydrogen chloride in an inert medium, to yield the corresponding 6-hydroxyhexanoic acid ester (a compound F). It is preferred to employ a large excess of the alcohol to serve as reaction medium. Preferred alcohols include methanol, ethanol and isopropanol. Elevated temperatures may be employed, e.g. 40° to 120°, preferably the reflux temperature of the mixture.

In process (f), a compound F is oxidized to its corresponding compound G. The reaction may be carried out in the conventional manner for oxidizing a primary alcohol to an aldehyde. A convenient method is by employing pyridinium chlorochromate under essentially anhydrous conditions in an inert medium, e.g., a chlorinated lower alkane, such as methylene chloride, at moderate temperatures, e.g., 20° to 50° C., conveniently at room temperature (20° to 30° C.). It is preferred to include molecular sieves in the reaction mixture.

In process (g), a compound G is converted to a compound H by reacting with a Wittig reagent of the formula III $$R-CH=P(R'') \qquad\qquad$$

in which R is as defined above, and $R^w$ is an aryl or alkoxy ($C_1$-$C_6$) radical. The reaction is conveniently carried out in an inert medium, e.g., a cyclic ether such as tetrahydrofuran at reduced temperatures, e.g. -15° to +5° C., such as -10° to 0° C. The reagent is prepared by treating a compound IV:

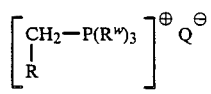

in which R and $R^w$ are as defined above and Q is a higher halo (having an atomic weight of from about 34 to 120), e.g., chloro, bromo or iodo, with a strong base, such as an alkali metal salt of a hydrocarbon, e.g., n-butyl lithium, in an inert medium, such as a cyclic ether, at reduced temperatures, e.g., from about -15° to 0° C., e.g., about -10° C.

In the Wittig reagent, when $R^w$ is aryl it is preferably phenyl which is unsubstituted or substituted by one or two lower alkyl ($C_1$-$C_4$) or chloro substituents, when $R^w$ is alkoxy, it is preferably ethoxy.

In process (h¹) a compound H is deprotected to the corresponding compound I'. Where the protecting group is a silyl-type, then acid treatment is employed, e.g., using a mixture of at least equal (e.g. 2 times) molar portions of acetic acid and tetrabutylammonium fluoride (TBAF) in THF, methanolic HCl, or fluoride anion reagents. Moderate temperatures may be employed, e.g., from about 20° to 60°, e.g., 20° to 30° C. Where the protecting group is of the benzyl-type, deprotection is achieved by reductive hydrogenation, by methods known in the art.

In process (h²) a compound I', i.e. the deprotected form of a compound H, is saponified. This is achieved by treatment with aqueous alkali metal base, e.g., sodium hydroxide, preferably in a watermiscible co-solvent, e.g. dioxane, at reduced temperatures, e.g. from about −5° to +10° C., such as in an ice bath. Where a product is desired in which $R^6$ is hydrogen, i.e., the free acid form, such is obtained by acidifying the salt form (where $R^6=M$) by conventional means, e.g., by acidifying with dilute hydrochloric acid.

Process h³ is accomplished by heating a compound I″ in which $R^6$−H, in an inert medium, e.g., an aromatic hydrocarbon such as toluene at from about 80° to 140° C., for example at the reflux temperature of the reaction medium.

Alternatively, a compound H may be directly converted to its corresponding compound I‴ by carrying out the procedure of process h¹ and heating e.g. at about 80° to 140°, e.g. at the refluxing temperature of the reaction medium, i.e. process h⁴.

Reagents and starting materials described herein, e.g., compounds A and B are known and obtainable by known means, or where not known, may be obtained by adaptation of methods reported in the literature for the preparation of known analogs; some compounds being commercially available.

The final products and intermediate compounds described herein may be recovered and refined, where such is desired, by conventional means, such as by crystallization, distillation or chromatographic techniques such as column or thin layer chromatography, e.g., silica gel column chromatography.

The following examples are illustrative of the invention. All temperatures are centigrade and room temperature is 20° to 30° C., unless indicated otherwise. The compounds I obtained by these examples are in essentially the trans isomeric form.

Where NMR characterization data is presented, the analysis is run in CDCl₃ and values given in ppm; digits in parenthesis are number of protons; and t=triplet, d=doublet, s=singlet, m=multiple and b is broad, and J is coupling factor, unless indicated otherwise.

Evaporations are done under vacuum employing minimal heating. Drying of organic phases is done over anhydrous sodium sulfate, unless indicated otherwise.

EXAMPLE 1

(E)-Trans-6(2-phenylethenyl)-4-hydroxy-tetrahydropyran-2-one, (a compound I‴)

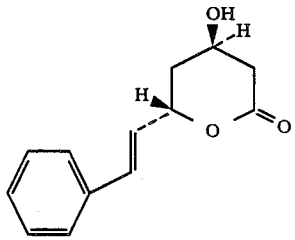

Step A, cis-1,3,5-tri-hydroxycyclohexane (a compound B)

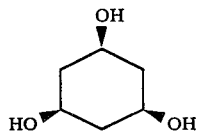

20 g (0.123 mol) of phloro-glucinol dihydrate is taken up in 200 ml of absolute ethanol followed by the addition of 10 g of W4 Raney nickel (freshly prepared according to the procedure described by R. L. Augustine in "Catalytic hydrogenation" [Marcel Dekker Inc.], p. 147). The mixture is hydrogenated at about 50° under about 50 psi for 24 hours.

The reaction mixture is then filtered on celite, the filtrate retained, and the solids washed with ethanol. The combined filtrate and washes are concentrated by evaporating to a small volume, to which 100 ml of acetone is added resulting in a clear solution, which is allowed to stand at room temperature, from which 7 g of cis product of this step crystallizes out—m.p. 181°.

Mixed (cis and trans) product can be recovered from the mother liquor by first concentrating it, then taking up in 50 ml of acetone plus enough methylene chloride to re-dissolve, and allowing product to crystallize out. This mixed product can be treated in the same manner as the compound B', in step B below and the product can then be used to prepare compound D via step C.

Step B, cis-1,3-di-(diphenyl-t-butyl-siloxy)-5-hydroxy-cyclohexane (a compound C)

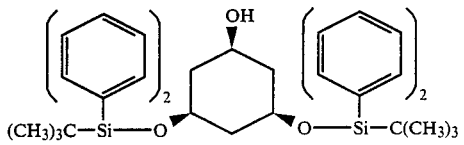

To a mixture of 1.32 g (10 mmol) of the triol product of Step A, and 4.08 g (60 mmol) of imidazol in 30 ml of DMF and 5.5 ml (20 mmol) of t-butyldiphenylsilyl chloride is added dropwise at 5° to 10° C. After the addition, the cooling is removed and the mixture is stirred at ambient temperature for 18 hours, then diluted with 200 ml of methylene chloride, and washed twice with 200 ml portions of water. The organic phase is dried, evaporated to dryness, and the residue chromatographed using hexane/ethyl acetate (4:1) as solvent system. The trisilated analog of the product of this step appears in the first fractions. The desired disilyl product (m.p. 108°–110° C., 2.6 g) appears in the second group of fractions.

Analysis of the product of this step shows the following:

IR(CHCl₃), 3609(OH), 3066, 3013, 2941, 2891, 2862, 1470, 1430, 1380, 1269, 1227, 1190, 1111, 1072, 1035, 938, 868 and 821 cm⁻¹.

NMR(CDCl₃): 1.00(s,18H); 1.17–1.59(m,4H), 1.95(m,3H), 3.02–3.42 (m,3H) and 7.20–7.60(m,20H) ppm.

Elemental Analysis: Found: C 74.90, H 8.00. Calc: C 74.95 H 7.94%.

Step C, cis-3,5-di-(diphenyl-t-butylsiloxy) cyclohexan-1-one (a compound D)

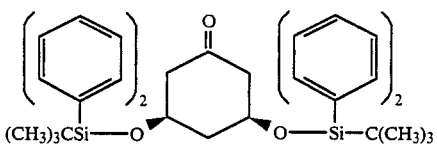

1.212 g (2 mmol) of the disyloxyalcohol product of Step B, above, 2.16 g (10 mmol) of pyridinium chlorochromate, 2 g of 3-Å molecular sieves and 15 ml of anhydrous methylenechloride are stirred in a round bottomed vessel for 2 hours at room temperature. The mixture is then filtered on silica, (the filtrate retained), and the silica washed with excess methylene chloride. The filtrate and silica wash are combined and evaporated to obtain a residue which is then chromatographed on a silica column, using hexane/ethyl acetate (2:1) as eluant system to yield the ketone product of this step (1.22 g, m.p. 108°–109°).

Analysis of the product shows the following characteristics:

IR(CHCl$_3$): 3066, 3016, 2949, 2865, 1713 (CO), 1470, 1430, 1380, 1256, 1232, 1109, 1077, 826 and 816 cm$^{-1}$.

NMR (CDCl$_3$): 1.02 (s,18H), 1.22–2.46(m, 6H), 3.55(m,2H) and 7.22–7.60 (m,20H) ppm.

Elemental Analysis: Found: C 75.20; H 7.60%. Calc: C 75.20; H 7.64%.

Step D, cis-2-oxy-4,6-di(diphenyl-t-butylsiloxy)cycloheptanone*, (a compound E)

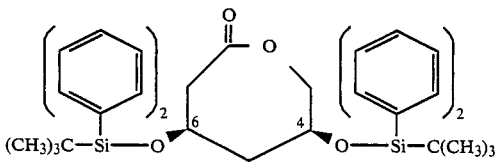

*May also be called cis3,5-di-diphenyl-t-butylsiloxy) 6-hydroxy hexanoic acid lactone.

To a solution of 32.2 g (53 mmol) of the ketone product of Step C, in 200 ml of dry methylenechloride are added 25.87 g (150 mmol) of m-chloroperbenzoic acid and 17.65 g (0.21 mol) of anhydrous sodium bicarbonate. The mixture is left in an ultrasound bath for 20 hours (during which period, refluxing starts). The mixture is cooled on ice, 100 ml of 10% Na$_2$S$_2$O$_3$ aq. solution is added and the contents diluted with 300 ml of methylenechloride. The aqueous phase is separated, and the organic phase washed once with 5% aq. sodium bicarbonate solution. The organic phase is dried and evaporated, to obtain an oily residue, which yields the title product of this step on recrystallization from n-pentane using a minimum amount of methylene chloride, m.p. 124°–125° (26.40 g).

The product shows the following characteristics on analysis:

IR(CHCl$_3$): 3048, 2997, 2949, 2865, 1901, 1834, 1739 (lactone C=O), 1591, 1472, 1432, 1385, 1272, 1190, 1109, 1072, 1011, 938, 868 and 795 cm$^{-1}$.

NMR (CDCl$_3$): 1.00 and 1.01 (2s,18H), 1.90 (m,1H), 2.20 (m,1H), 2.75 (m,1H), 2.95 (dd, J$_1$=10, J$_2$=14 Hz, 1H), 3.45–3.75 (m,2H), 3.93–4.17 (m,2H), 7.25–7.58 (m,20H) ppm.

Elemental Analysis: Found: C 72.90 H 7.40. Calc: C 73.27 H 7.44%.

Step E, methyl erythro-3,5di-(diphenyl-t-butylsiloxy)-6-hydroxy-hexanoate (a compound F)

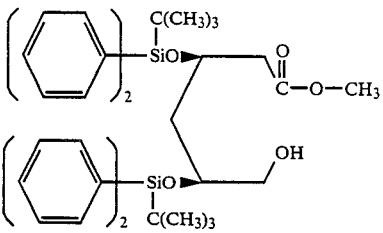

A solution of 1.2 g (1.9 mmol) of the lactone product of Step D above, in 50 ml of methanol and 0.5 ml of trifluoroacetic acid is refluxed for 30 minutes. The mixture is then evaporated to obtain a residue which is then chromatographed on a silica column, using hexane: ethyl acetate (3:1) as eluant, to recover 1.2 g of the title product of this step (as an oil) having the following characteristics:

IR(CHCl$_3$): 3580 (OH)m 1735 (ester CO) cm$^{-1}$.

NMR (CDCl$_3$): 0.95 (s,9H), 1.00 (s,9H), 1.68(b, 1H), 1.85 (t, J=7 HZ, 2H), 2.30 (d, J=7 HZ, 1H) and 7.25–7.67 (m, 20H) ppm.

Elemental Analysis: Found: C 71.30 H 7.40. Calc: C 71.52 H 7.69%.

Step F - Methyl erythro-3,5-di-(diphenyl-t-butylsiloxy)-6-oxo-hexanoate - a compound G)

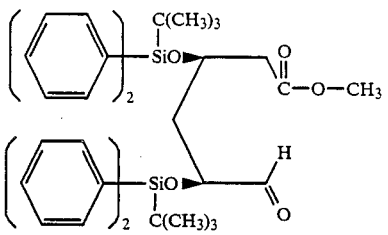

To a solution of 1.10 g (1.68 mmol) of the alcohol product of Step E above, and 1.08 g (5 mmol) of pyridinium chlorochromate in 20 ml of dry methylene chloride is stirred with 2 g of 3-Å molecular sieves for 4 hours. The mixture is then filtered through silica gel and and the filtrate is evaporated to yield the title product of this step as a residue (an oil; 1.10 g), which has the following characteristics on analysis:

IR (CHCl$_3$): 1735 (ester and aldehyde C=O).

NMR (CDCl$_3$): 0.98 (s,3H), 1.05 (s,3H), 1.95 (t, J=5.67 Hz, 2H), 2.33 (d,J=5.67 Hz, 2H), 3.50 (s,3H), 4.10 (t, J=5.67 Hz, 1H), 4.45 (m,1H), 7.25–7.75 (m, 20H) and 9.40 (s, 1H) ppm.

Step G, (E)-methyl erythro-3.5-di-(diphenyl-t-butylsiloxy)-7phenyl-hept-6enoate (a compound H)

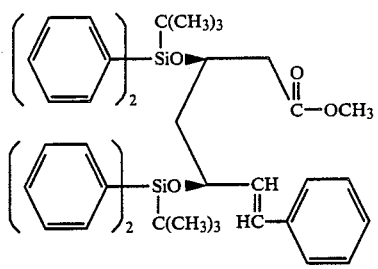

0.28 g (0.72 mmol) of benzyltriphenylphosphonium chloride is suspended in 2 ml of dry tetrahydrofuran (THF) and 0.4 ml of 1.55 M solution of n-butyl lithium (in THF) is added at $-10°$. The mixture is stirred at the reduced temperature for 40 minutes. To the resulting orange-colored solution, is added 0.47 g (0.72 mmol) of the aldehyde product of Step F (above) in 2 ml of dry THF. The resulting mixture is maintained at 0° for 18 hours, and then diluted with 50 ml methylene chloride, washed with water, the organic phase separated and dried and a residue obtained by evaporation.

The residue is chromatographed on silica using hexane: ethyl acetate (4:1) as eluant system to obtain 403 mg of the olefinic title product of this step (as an oil) showing the following characteristics on analysis:

IR(CHCl$_3$): 3063, 3021, 2947, 2862, 1734 (ester CO), 1599, 1432, 1374, 1266, 1216, 1172, 1106, 829 and 780 cm$^{-1}$.

NMR (CDCl$_3$): 0.95 (s,9H), 1.00 (s,9H), 1.78 (m,1H), 1.98 (m,1H), 2.38 (dd, $J_1=7$ and $J_2=15$ Hz, 1H), 2.50 (dd, $J_1=7$, $J_2=15$ Hz, 1H), 3.52 (s, 3H), 4.33 (m,2H), 5.80 (dd, J=16 Hz, 2H) and 6.98–7.70 (m, 25H) ppm.

Elemental Analysis: Found: C 75.50 H 7.20 . Calc: C 75.99 H 7.49%.

Step H$^1$, (E)-methyl erythro-3,5-dihydroxy-7-phenyl-hept-6-enoate (a compound I')

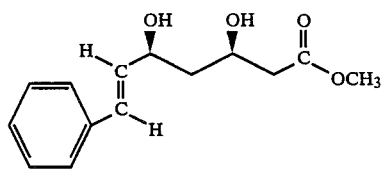

A solution of 455 mg (0.63 mmol) of the diprotected-olefinic product of Step G, above, 0.3 ml (5 mmol) of glacial acetic acid, and 5 ml (5 mmol) of 1M tetrabutylammonium fluoride (TBAF) solution in THF, is stirred at room temperature for 18 hours. The mixture is then diluted with 100 ml of methylene chloride, washed with water, the organic phase separated, dried, evaporated and the residue chromatographed on silica gel using ethyl acetate as eluant. The title product of this step is recovered as an oil (70 mg) having the following characteristics on analysis:

NMR (CDCl$_3$), 1.75 (m,2H), 2.53 (m,2H), 3.38 (b,1H), 3.70 (s,3H), 3.83 (b,1H), 4.35 (br,1H), 4.60 (b,1H), 6.23 (dd, $J_1=16$, $J_2=7$Hz,1H), 6.69 (d, J=16 Hz, 1H) and 7.20–7.45 (m, 5H) ppm.

Step H$^2$ (E)-trans-6-(2-phenylethynyl)-4-hydroxytetra-hydropyran-2-one 60 m.g. (0.24 mmol) of the dihydroxy ester product of step H$^1$ is dissolved in 1 ml of dioxane, and the solution cooled in an ice bath. 0.3 ml of 1N sodium hydroxide is then added. After 10 minutes the mixture is acidified (with dilute hydrochloric acid), and then extracted with two 10 ml portions of methylene chloride. The extract is taken to dryness by evaporating, and the resulting residue refluxed in toluene for 5 hours. The mixture is then evaporated and the resulting residue chromatographed on silica gel, eluting with ethyl acetate. The title product is recovered (43 mg) having a melting point of 94°–95°. Analysis shows the following characteristics for the product:

IR (CHCl$_3$): 3609, 3048, 2992, 2926, 1734, 1599, 1364, 1248, 1161, 1048 and 970 cm$^{-1}$.

NMR (CDCl$_3$). 1.62 (b,1H), 1.95 (m,1H), 2.13 (m,1H), 2.68 (m,1H), 2.83 (dd, $J_1=17$, $J_2=5$ Hz,1H), 4.45 (m,1H), 5.38 (m,1H), 6.23 (dd, J=16 and 7 Hz,1H), 6.73 (d, J=16 Hz, 1H) and 7.25–7.44 (m,5H) ppm.

Elemental Analysis: Found: C: 71.30 and, H:6.20%. Calc: C: 71.54 H:6.47%.

EXAMPLE 2

(E)-Sodium erythro-3,5-dihydroxy-7-(2'-[4''-fluorophenyl]naphth-1-yl)hept-6-enoate

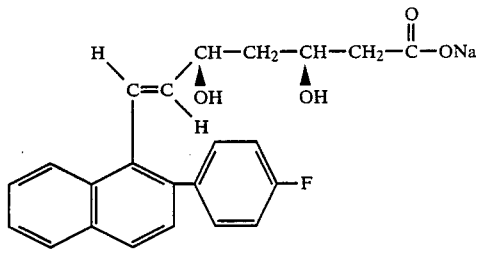

Step A (E)-methyl erythro-3,5-di-(diphenyl-t-butylsiloxy)-7-(2'-[4''-fluorophenyl]naphth-1'-yl)hept-6-enoate (a compound I')

Repeating the procedure of Step G of Example 1, but employing 555 mg (0.85 mmol) of the aldehyde-ester product of Step F of Example 1 and 450 mg (0.85 mmol) of 1-[2'-(4''-fluorophenyl)-naphth-1-yl] methyl triphenyl phosphonium chloride, and 0.55 ml of 1.55 M butyllithium solution, there is obtained the title olefinic product of this step which is recovered by chromatography (430 mg) having the following characteristics on analysis:

IR (CHCl$_3$): 3055, 2949. 2864, 2350, 2334, 1736(ester CO), 1601, 1506, 1469, 1435, 1374, 1247, 1197, 1163, 1108, 828, 800 and 672 cm$^{-1}$.

NMR (CDCl$_3$): 0.89 (s,9H), 0.93 (s,9H), 1.70 (m,2H), 2.30, (m,1H), 2.50 (m,1H), 3.58 (s,3H), 4.25 (m,1H), 4.40 (m,1H) 5.23 (dd, J=16 and 5 Hz,1H), 6.31 (d, J=16Hz,1H), 6.88–7.90 (m,30H) ppm.

Analysis: Found: C 77.00, H 6.80. Calc: C 77.19, H 6.82%.

Step B Sodium trans-3,5-dihydroxy-7-(2'-[4''-fluorophenyl]-napht-1-yl)hept-6-enoate 400 mg (0.47 mmol) of the di-protected olefinic product of Step A of this example is deprotected using tetrabutylammonium fluoride according to the procedure of Step H¹ of Example 1, to obtain the corresponding Compound I' (92 mg) which is treated with 1 equivalent of 1N sodium hydroxide solution in dioxane, the mixture washed with ether, and the aqueous phase is retained and on lyophilisation yields 88 mg of the product of this Example as an amorphous colorless solid, which upon analysis is characterized as follows:

IR (KBr): 1580 (COONa) cm⁻¹

NMR (D₂O): 1.20 (m,1H), 1.45 (m,1H), 2.13 (m,2H), 3.44 (m,1H), 4.13 (m,1H), 5.23 (dd, J=16 and 6Hz, 1H), 6.58 (d, J=16 Hz, 1H), and 6.85–8.00 (m, 10H) ppm.

EXAMPLE 3

(E)-Sodium erythro-7-[1'-methyl-3'-(4''-fluorophenyl)indol-2'-yl]-3,5-dihydroxyhept-6-enoate

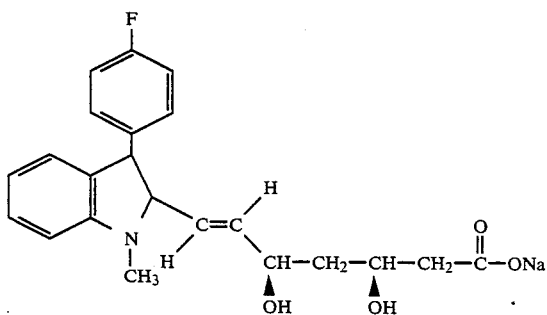

Step A, (E)-Methyl-erythro-7-[1'-methyl-3'-(4''-fluorophenyl)indol-2'-yl]-3,5 di-(diphenyl-t-butylsiloxy)-hept-6-enoate Following the procedure of Step G of Example 1, but using 0.59 g (0.90 mmol) of the aldehyde-ester (a compound F) of Step F of Example 1, and 482 mg (0.90 mmol) of [1'-methyl-3'-(4''-fluorophenyl)indol-2'-yl]methyl-triphenyl phosphonium chloride, and treatment with a solution of butyl lithium the title di-protected olefinic ester of this step is obtained (366 mg) which upon analysis is characterized as follows:

NMR (CDCl₃): 0.85 (s,9H), 0.95 (s,9H), 1.75 (m,2H), 2.38 (m,1H), 2.55 (m,1H), 3.33 (s,3H), 3.53 (s,3H), 4.23 (m,1H), 4.35 (m,1H), 5.45 (dd, J=16 and 6Hz, 1H), 6.10 (d, J=16 Hz, 1H), 6.90–7.75 (m, 28H) ppm.

Step B, (E)-sodium erythro-7-[1'-methyl-3-(4''-fluorophenyl)indol-2'-yl]3,5-dihydroxyhept-6-enoate 400 mg (0.49mmol) of the di-protected ester obtained in Step A of this example is treated with TBAF as described in Step H¹ of Example 1, above, to obtain the corresponding diol-ester (a compound I') which upon treatment with an equivalent of 1N sodium hydroxide followed by lypholization, yields the title sodium salt product of this example (59 gm), which is characterized as follows:

IR (KBr): 1580, 1508, 1405, 1220, 1160, 1120, 1080, 980, 820, 750 cm⁻¹.

EXAMPLE 4

Repeating the procedure of Example 1, but in Step E employing in place of the methanol used therein, an approximately equivalent amount of
(a) ethanol; or
(b) isopropanol;
there is accordingly obtained the analogous:
(a) ethyl; and
isopropyl esters of the products of Steps E, F, G and H¹ of Example 1.

EXAMPLE 5

(E)-Trans-6(2-phenylethenyl)-4-hydroxy-tetrahydropyran-2-one

A solution of 91 mg (0.13 mmol) of the di-protectedolefinic product of step G, * 0.06 ml (1 mmol) of glacial acetic acid and 1 ml (1 mmol) of 1M TBAF solution in THF, is stirred at room temperature for 18 hours, followed by heating the mixture for 2 hrs. at 80° C. The mixture is diluted with 20 ml of CH₂Cl₂, washed with water the organic phase separated, dried, evaporated, and the residue chromatographed on silica gel using ethyl acetate as eluant. The title product of this example (14 mg) is isolated, m.p. 94°–95° C.

\* of Example 1.

EXAMPLE 6

Repeating the procedure of Example 5, but using in place of the methyl erythro-3,5-di-(diphenyl-t-butylsiloxy-7-phenyl-hept-6-enoate used therein, an approximately equivalent amount of:

(a) (E)-methyl erythro-3,5-di-(diphenyl-t-butylsiloxy)-7-(2'-[4''-fluorophenyl]-naphth-1-yl)hept-6enoate; (product of Step A of Example 2); or (b) (E)-methyl erythro-7-[1'methyl-3-(4''-fluorophenyl)indol-2'-yl]-3,5-di-(diphenyl-t-butylsiloxy)-hept6-enoate, (product of Step A of Example 3;

there is accordingly obtained the corresponding compounds I''':

(a) (E)-trans-6-(2'-[2''-(4'''-fluorophenyl)naphth-1''-yl]ethenyl)-4-hydroxy3,4,5,6-tetrahydro2H-pyran-2-one; and (E)-trans-6-[1'-methyl-3'-(4''-fluorophenyl)indol-2'-ylethenyl]-3,4,5,6-tetrahydro-4hydroxy-2H-pyran-2-one, respectively.

What is claimed is:

1. A compound of the formula:

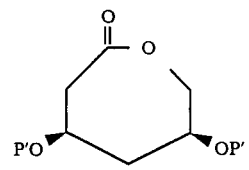

wherein each P' is an hydroxy group-protecting group selected from the group consisting of tri-substituted silyl, benzyl, and substituted benzyl.

2. A compound according to claim 1 wherein each substituent of each tri-substituted silyl is selected from the group consisting of C₄–C₈ tertiary alkyl; phenyl; phenyl substituted by 1 or 2 substituents selected from C₁–C₄ alkyl, chloro, nitro and trifluoromethyl; and phenyl monosubstituted in the para position by phenyl, benzyl, or phenyl or benzyl substituted by 1 or 2 substituents selected from $C_{1-4}$alkyl, chloro, nitro and trifluoromethyl.

3. A compound according to claim 1 wherein the benzyl is substituted by 1 or 2 substituents selected from $C_1-C_4$ alkoxy, chloro, nitro and $C_1-C_6$ alkyl or is monosubstituted in the para position by phenyl, benzyl or phenyl or benzyl substituted by 1 or 2 substituents selected from $C_{1-4}$alkoxy, chloro, nitro and $C_{1-6}$alkyl.

4. A compound according to claim 3 wherein each substituent of each tri-substituted silyl is selected from the group consisting of $C_4-C_8$ tertiary alkyl; phenyl; and phenyl substituted by 1 or 2 substitutents selected from $C_1-C_4$ alkyl, chloro, nitro and trifluoromethyl; phenyl monosubstituted in the para position by phenyl, benzyl or phenyl or benzyl substituted by 1 or 2 substituents selected from $C_{1-4}$alkyl, chloro, nitro, and trifluoromethyl.

5. The compound according to claim 1 which is cis-2-oxa-4,6-di-(diphenyl-t-butylsilyloxy)cycloheptanone.

6. A compound of formula E

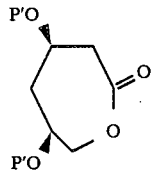

wherein each P' is a protective group for a hydroxy function.

* * * * *